United States Patent
Rees et al.

(10) Patent No.: US 10,344,339 B2
(45) Date of Patent: Jul. 9, 2019

(54) MYCOBACTERIA DETECTION USING BACTERIOPHAGES

(71) Applicant: THE UNIVERSITY OF NOTTINGHAM, Nottingham (GB)

(72) Inventors: Catherine Rees, Nottingham (GB); Benjamin Swift, Nottingham (GB)

(73) Assignee: THE UNIVERSITY OF NOTTINGHAM, Nottingham (GB)

( * ) Notice: Subject to any disclaimer, the term of this patent is extended or adjusted under 35 U.S.C. 154(b) by 0 days.

(21) Appl. No.: 15/026,720

(22) PCT Filed: Oct. 1, 2014

(86) PCT No.: PCT/GB2014/052970
§ 371 (c)(1),
(2) Date: Jul. 1, 2016

(87) PCT Pub. No.: WO2015/049516
PCT Pub. Date: Apr. 9, 2015

(65) Prior Publication Data
US 2016/0312269 A1 Oct. 27, 2016

(30) Foreign Application Priority Data

Oct. 1, 2013 (GB) .................................... 1317392.7
Nov. 22, 2013 (GB) .................................... 1320613.1

(51) Int. Cl.
*C12Q 1/689* (2018.01)
*C12Q 1/6806* (2018.01)

(52) U.S. Cl.
CPC .......... *C12Q 1/689* (2013.01); *C12Q 1/6806* (2013.01)

(58) Field of Classification Search
None
See application file for complete search history.

(56) References Cited

FOREIGN PATENT DOCUMENTS

WO WO2008129419 * 11/2008 ............... C12Q 1/24

OTHER PUBLICATIONS

GenBank: X16293.1. *Mycobacterium paratuberculosis* insertion element IS900. (Year: 1999).*
Stanley et al. Development of a new, combined rapid method using phage and PCR for detection and identification of viable *Mycobacterium paratuberculosis* bacteria within 48 hours. Appl Environ Microbiol. Mar. 2007;73(6):1851-7. (Year: 2007).*

(Continued)

*Primary Examiner* — Michelle S Horning
(74) *Attorney, Agent, or Firm* — Baker Donelson

(57) ABSTRACT

A method for testing for target Mycobacteria in a reaction mixture comprising the steps of: providing a reaction mixture; admixing a bacteriophage with the reaction mixture under conditions suitable to allow the bacteriophage to infect any target Mycobacteria present in the reaction mixture; allowing time for the bacteriophage to lyse infected live target Mycobacteria; and analysing in said reaction mixture DNA from the lysed Mycobacteria to identify a signature DNA sequence that occurs in the target Mycobacteriumspedes.

16 Claims, 12 Drawing Sheets

Figure 1:
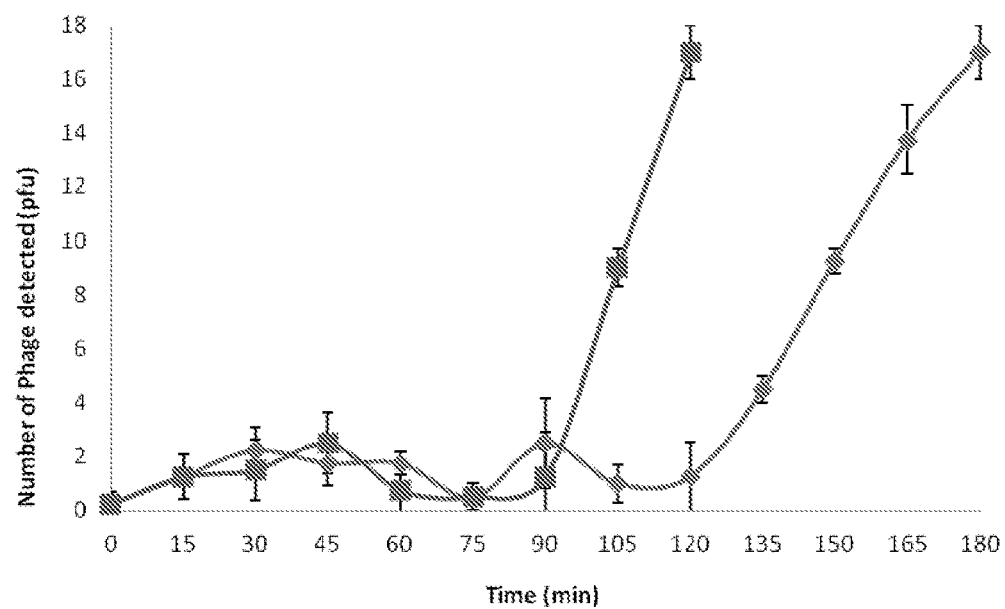

Specification includes a Sequence Listing.

(56) References Cited

OTHER PUBLICATIONS

Swift Benjamin M C et al: "Development of a rapid phage-based method for the detection of viable *Mycobacterium avium* subsp. *paratuberculosisin* blood within 48 h", Journal of Microbiological Methods, vol. 94, No. 3, Jun. 25, 2013 (Jun. 25, 2013) ,pp. 175-179, XP028700679, ISSN: 0167-7012, DOI:10.1016/J.MIMET.2013.06. 015.
Botsaris George et al: "Detection of *Mycobacterium avium* subsp. *paratuberculosis* in bulk tank milk by combined phage-PCR assay: Evidence that plaque number is a good predictor of MAP" , International Journal of Food Microbiology, Elsevier BV, NL, vol. 164, No. 1,Apr. 3, 2013 (Apr. 3, 2013), pp. 76-80, XP028531627, ISSN: 0168-1605, 001:10.1016/J.IJFOODMICRO.2013.03.023.
"FASTPlaqueTB (TM)", Jan. 1, 2004 (Jan. 1, 2004), pp. 1-15, XP055168514, Retrieved from the Internet: URL:http://www.cosmosbiomedical.com/PDF/biotecproducts/FASTPlaqueTB IFU Rev 4 Specimen copy.pdf—[retrieved on Feb. 9, 2015].
International Search Report; dated Feb. 9, 2015.
Written Opinion of the International Searching Authority.
Midgley, Olivia; "New 'highliy sensitive' bovine TB test approved by APHA"; May 22, 2018; Farmers Guardian.
Hurley, Sarah S., G. A. Splitter, and R. A. Welch. "Rapid lysis technique for mycobacterial species." Journal of clinical microbiology 25.11 (1987): 2227-2229.

\* cited by examiner

SEQ ID NO 1 - IS900 Signature Sequence
TCCTTACCTTTCTTGAAGGGTGTTCGGGGCCGTCGCTTAGGCTTCGAATTGCCCAGGGAC
GTCGGGTATGGCITTCATGTGGTTGCTGTGTTGGATGGCCGAAGGAGATTGGCCGCCCGC
GGTCCCGCGACGACTCGACCGCTAATTGAGAGATGCGATTGGATCGCTGTGTAAGGACAC
GTCGGCGTGGTCGTCTGCTGGGTTGATCTGGACAATGACGGTTACGGAGGTGGTTGTGGC
ACAACCTGTCTGGGCGGGCGTGGACGCCGGTAAGGCCGACCATTACTGCATGGTTATTAA
CGACGACGCGCAGCGATTGCTCTCGCAGCGGGTGGCCAACGACGAGGCCGCGCTGCTGGA
GTTGATTGCGGCGGTGACGACGTTGGCCGATGGAGGCGAGGTCACGTGGGCGATCGACCT
CAACGCCGGCGGCGCCGCGTTGCTGATCGCCTTGCTCATCGCTGCCGGGCAGCGGCTGCT
TTATATTCCCGGGCGCACGGTCCATCACGCCGCGGGTAGTTACCGCGGCGAAGGCAAGAC
CGACGCCAAAGACGCTGCGATCATCGCCGATCAGGCCCGGATGCGCCACGACTTGCAGCC
TCTGCGCGCCGGCGATGACATCGCAGTCGAGCTGCGCATCCTGACCAGCCGACGTTCCGA
TCTGGTGGCTGATCGGACCCGGGCGATCGAACCGAATGCGCGCCCAGCTGCTGGAATACT
TTCXMCGCTGGAACGCGCCTTCGACTACAACAAGAGCCGTGCCGCGCTGATCCTGCTTAC
TGGCTACCAAACTCCCGACGCGCTGCGCAGCGCCGGTGGCGCTCGAGTAGCCGCGTTCTT
GCGTAAACGCAAGGCCCGCAACGCCGATACCGTCGCAGCCACCGCGCTGCAGGCCGCTAA
CGCCCAACACAGCATCGTGCCCGGCCAACAACTGGCGGCCACTGTGGTGGCCCGCCTGGC
CAAGGAGGTGATGGCCCTCGACACCGAAATCGGCGACACCGACGCGATGATCGAGGAGCG
ATTTCGCCGCCACCGCCACGCCGAAATCATCCTGAGCATGCCCGGATTCGGCGTCATCCT
GGGCGCTGAGTTCCTCGCCGCCACCGGCGGGGACATGGCCGCATTCGCCTCCGCCGACCG
CCTCGCCGGCGTCGCCGGCCTGGCGCCGGTACCACGAGATTCCGGCCGCATCAGCGGAAA
CCTCAAACGCCCCCGACGCTACGACCGGCGCCTGCTGCGCGCCTGCTACCTGTCGGCCTT
GGTCAGCATCCGCACCGACCCCTCCTCGCGCACCTACTACGACCGAAAACGCACCGAAGG
AAAACGCCACACCCAAGCCGTCCTCGCCCTGGCCCGCCGCCGCCTCAACGTCCTGTGGGC
CATGCTGCGCGACCACGCTGTCTACCACCCCGCAACCACTACCGCGGCGGCTTGACAACG
TCATTGAGAAT

Figure 11

| | Agreement between each tests (%) | | | |
|---|---|---|---|---|
| | One Day Vs Phage Assay | One Day Vs Blood PCR | One Day vs PCR and Phage | Phage vs PCR |
| Month 6 | 64 | 27 | 27 | 64 |
| Month 7 | 55 | 55 | 36 | 64 |
| Month 8 | 82 | 64 | 55 | 64 |

MYCOBACTERIA DETECTION USING BACTERIOPHAGES

This application is a National Stage Application under 35 U.S.C. section 371 of PCT/GB2014/052970 filed Oct. 1, 2014, which claims priority from and the benefit of GB Application No: 1317392.7 filed Oct. 1, 2013, and GB Application No: 1320613.1 filed Nov. 22, 2013, the entire contents of each application are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jan. 2, 2015, is named 2936619- 001-US1_SL.txt and is 2,867 bytes in size.

This invention relates to a method for detecting viable Mycobacteria. It also relates to reagents for use in the method.

Detecting Mycobacteria is of interest for a variety of applications. It is particularly useful to be able to detect the presence of the organism in people or animals for the diagnosis of mycobacterial infections. Rapid and reliable detection of infection by Mycobacteria is important for controlling disease, and the ability to use high-throughput techniques allows screening of large numbers of samples. It would be of great value, for example, to provide high-throughput screening that could rapidly and reliably test samples from individual animals within a herd of cattle for *Mycobacterium bovis* (Bovine TB) or *Mycobacterium avium* subsp. *paratuberculosis* (MAP), both of which are endemic diseases of cattle in the UK. Both organisms can be detected in the blood of animals exposed to MAP, even when they are in the sub-clinical stage of disease. The rapid and reliable detection of these organisms within a herd is very important step in control of disease.

Current rapid methods for detection of viable Mycobacteria are able to detect and enumerate viable MAP in blood within two days. However the method used is labour intensive and would be difficult to scale up for high-throughput analysis of samples. In a veterinary setting, where animals from a whole herd need to be tested, often hundreds of samples need to be tested at the same time, and current methods are too costly and labour-intensive to make large scale testing practicable.

The current clinical standard tests for TB are antibody-based (immune response) tests. The problem with these is that they detect the response of the host immune system to the organism rather than detecting viable organisms. The sensitivity of these tests is known to be low when used as a diagnostic, requiring repeat results or advances stages of infection before a clear positive result is gained. A particular disadvantage of antibody-based tests is that these tests also do not distinguish between infected and vaccinated animals.

In previous PCR-based methods for detecting Mycobacteria the sensitivity of the assay is limited by ability to recover DNA from the Mycobacteria which are physically robust and difficult to lyse.

In addition previous PCR-based methods do not easily differentiate between live and dead cells. In the food industry especially, the ability to differentiate between live and dead Mycobacteria is very important since processed food may still contain the DNA of inactivated cells. Potentially the ability to distinguish between live and dead Mycobacteria is also important in clinical diagnostics using blood samples, since dead cells within macrophages would also be detected, even if the animal was recovering from infection.

Many of the major disease-causing Mycobacteria such as *Mycobacterium avium* subsp. *paratuberculosis* (MAP), *Mycobacterium tuberculosis, Mycobacterium bovis* are slow-growing and therefore difficult to culture. The length of time that it takes to culture these species makes it difficult to use cultures in a diagnostic test for infection.

It would be advantageous to provide a specific and sensitive method of detecting viable Mycobacteria, and in particular a method which could be performed in a 'single-tube' format that has the potential to be automated to allow rapid and cost effective testing of large sample numbers. It would be particularly advantageous to provide a test that could differentiate between infected and vaccinated individuals.

In a first aspect the present invention provides a method for testing for target Mycobacteria in a reaction mixture comprising the steps of:
  a) providing a reaction mixture;
  b) admixing a bacteriophage with the reaction mixture under conditions suitable to allow the bacteriophage to infect any target Mycobacteria present in the reaction mixture;
  c) allowing time for the bacteriophage to lyse infected live target Mycobacteria;
  e) analysing DNA from the lysed Mycobacteria to identify a signature DNA sequence that occurs in the target *Mycobacterium* species.

The method may further comprise the step d) separating any unlysed cells from the reaction mixture. Step d) separating any unlysed cells from the reaction mixture may be performed between steps c) and e).

In another aspect the present invention provides a method for testing for target Mycobacteria in a reaction mixture comprising the steps of:
  a) providing a reaction mixture;
  b) admixing a bacteriophage with the reaction mixture under conditions suitable to allow the bacteriophage to infect any target Mycobacteria present in the reaction mixture;
  c) allowing time for the bacteriophage to lyse infected live target Mycobacteria;
  d) separating any unlysed cells from the reaction mixture
  e) analysing DNA from the lysed Mycobacteria to identify a signature DNA sequence that occurs in the target *Mycobacterium* species.

The bacteriophage used may be selected because it is a bacteriophage that specifically infects the target Mycobacterial strain to be detected. The bacteriophage used may be selected because it is a broad host range bacteriophage and infects a range of Mycobacterial strains including the target Mycobacterial strain. The bacteriophage used may not be specific for the target Mycobacterial strain but may infect a range of bacterial strains.

Bacteriophages are only able to lyse viable cells (also called replication competent cells). Viable Mycobacteria in a sample allow the bacteriophage to replicate which eventually results in host cell lysis. However non-viable Mycobacteria cannot support the bacteriophage replication and are not lysed by the bacteriophage. This allows the method to distinguish between samples that contain viable target Mycobacteria and samples that contain non-viable target Mycobacteria.

Unlysed Mycobacterial cells may be removed from the reaction mixture between steps c) and e). Unlysed Mycobacteria may be removed from the reaction mixture by any suitable method.

Unlysed Mycobacteria may be removed from the reaction mixture by centrifugation, filtration or by barrier methods such as spin columns.

Alternatively, substantially all the Mycobacteria (viable and non-viable) in a reaction mixture may be bound to a substrate prior to the addition of the bacteriophage. Then following addition of the bacteriophage and lysis of any bound viable Mycobacteria, the substrate may then be removed, thereby removing any unlysed (non-viable) Mycobacteria. The substrate may be, for example, a chromatography column or magnetic beads or other material coated with a polypeptide that specifically binds to the target Mycobacteria.

The reaction mixture may be any sample suspected of containing Mycobacteria. For example, the reaction mixture may be a blood or tissue sample or a sample of food or animal feed. The reaction mixture may be made by mixing or dissolving a sample suspected of containing Mycobacteria in a solvent, buffer solution. The reaction mixture may be prepared using a substrate that can be mixed with a sample suspected of containing Mycobacteria and then removing the substrate from the sample with any Mycobacteria present stuck to the substrate. The substrate can then be contacted with, mixed with, or dissolved in a liquid to provide the reaction mixture.

The reaction mixture may be prepared by a method comprising the steps of:
  i) providing a sample suspected of comprising a target Mycobacterial cell;
  ii) providing a substrate that specifically binds to the target Mycobacterial cell;
  iii) contacting the sample with a substrate under conditions suitable to cause the target Mycobacterial cell to bind to the substrate; and
  iv) removing the substrate and any bound Mycobacteria from the sample; and
  v) providing a reaction mixture comprising the substrate and any bound Mycobacteria.

The substrate may be any substrate, for example a substrate that can support a biotin-avidin binding system. The substrate may, for example be magnetic beads, rod magnets or a surface such as the bottom of a 96-well plate. The substrate may be made to specifically bind to the target Mycobacterial cell by coating it with a substance that specifically binds to the target Mycobacteria, for example the substrate may be coated with a peptide that specifically binds to the target Mycobacteria. The substrate may be coated with an antibody that specifically binds to the target Mycobacteria.

The target Mycobacterial cell may be any species belonging to the genus *Mycobacterium*, for example *Mycobacterium avium* subsp. *paratuberculosis* (MAP), *Mycobacterium tuberculosis*, *Mycobacterium bovis* in *Mycobacterium leprae*, *Mycobacterium avium*. The target Mycobacterial cell may belong to any Mycobacterial species of interest.

The target Mycobacterial cell may be *Mycobacterium avium* subsp. *paratuberculosis* strain K10, or B4.

The bacteriophage may be any lytic bacteriophage that is able to infect and lyse the target Mycobacteria. The bacteriophage may be specific to the target Mycobacteria. The bacteriophage may be any broad host range mycobacteriophage that is able to infect and lyse the target Mycobacteria. For example the bacteriophage may be D29 or TM4 bacteriophage.

The bacteriophage may only lyse live target Mycobacteria. The bacteriophage may not lyse dead or non-viable Mycobacteria.

DNA from the lysed *Mycobacterium* may be analysed by any suitable technique to identify signature sequences that are found in the target mycobacterial cell. The reaction mixture may be analysed to identify signature sequences from one or more than one different target Mycobacteria, for example from one or two different target Mycobacteria, or three different target Mycobacteria, or four different target Mycobacteria, or five different target Mycobacteria, or six different target Mycobacteria, or seven different target Mycobacteria, or eight different target Mycobacteria, or nine different target Mycobacteria, or ten different target Mycobacteria or more. The DNA may be analysed by PCR using primers that anneal, allow amplification, specifically to a signature DNA sequence that occurs in the target Mycobacterial cell or each of the target Mycobacterial species.

The DNA may be analysed by PCR using primers that anneal specifically to a signature DNA sequence that occurs in the target Mycobacterial cell or each or the target type of Mycobacteria. The signature DNA sequence may be a sequence having at least 60% identity, at least 70% identity, at least 80% identity, at least 90% identity, at least 95% identity, 98% identity or 100% identity to SEQ ID No. 1. The primers may anneal specifically to the signature DNA sequence and/or may allow amplification of the specific signature DNA. The forward primer may, for example, have the sequence 5'-CAG CGG CTG CTT TAT ATT CC-3' (SEQ ID NO: 2) and/or the reverse primer may, for example have the sequence 5'-GGC ACG GCT CTT GTT GTA GT-3' (SEQ ID NO: 3).

To increase the specificity more than one, more than two, more than three, more than four, more than five, more than six, more seven or more than eight signature sequences may be considered for each Mycobacteria to be detected.

The signature DNA sequence may be the insertion element IS900 (SEQ ID NO: 1 shown in FIG. 11) or the unique gene sequence f57 for *Mycobacterium avium* subsp. *paratuberculosis* (MAP).

The DNA melting step in the PCR may be carried out at a temperature that does not lyse Mycobacterial cells. If the DNA melting step of the PCR is carried out at a temperature that does not lyse the Mycobacterial cells then unlysed Mycobacterial cells do not need to be removed from the reaction mixture before the PCR step. The DNA melting step in the PCR may be carried out at less than 92° C., at less than 93° C., at less than 94° C. or at less than 95° C.

The sample may be a sample from an animal or human suspected of being infected with the target *Mycobacterium*.

The sample may be a sample of blood, body fluid or tissue. The sample may be a sample of blood, serum, sputum, milk, saliva, urine, faeces. The sample may be a sample of a product for human or animal consumption. For example the sample may be a sample of milk, cheese or a dairy product containing raw milk.

The method may be performed in one reaction vessel, for example one test tube, one microcentrifuge tube or one well of a multiwell plate. Steps a) to e) of the method may be performed in one reaction vessel. It is advantageous that the method may be performed in one reaction vessel because it allows the method to be done as a high throughput screening method. The method may be a high throughput screening method. This is advantageous if a large number of samples need to be tested, for example if a herd of cattle needs to be tested for bovine TB.

The method may be performed within 24 hours or within 48 hours. Steps a) to e), and in particular steps a) to c), of the method may be performed within 24 hours or within 48 hours. This is advantageous because it can be determined whether there are live or viable Mycobacteria in a sample within 24 hours or within 48 hours. Preferably results can be obtained in less than 48 hours, less than 24 hours, less than 12 hours, less than 10 hours, less than 8 hours, less then 6 hours, or 5 hours or less.

The method may comprise the use of antibodies, for example antibodies may be used as a capture agent to bind unlysed cells.

The method may not comprise the use of antibodies. The method may not comprise the use of antibodies for identifying Mycobacteria or mycobacterial infection. The method may comprise the use of antibodies as a capture agent to bind unlysed cells but not for identifying Mycobacteria or mycobacterial infection.

The method of the invention would be able to distinguish between an individual that had been vaccinated against a *Mycobacterium* and an individual that had been infected with the *Mycobacterium*. This allows vaccination of the animals, for example humans and cows against Mycobacteria to be carried out and a test still to be available to detect mycobacterial infection. Previous methods for detecting Mycobacteria that use anti-mycobacterial antibodies produced by an infected individual as markers of infection cannot be used on animals that have been vaccinated because the immune reaction to the vaccine produces antibodies that may be detected by these tests. The present method can distinguish between an infected animal and a vaccinated animal because it does not detect antibodies but rather detects viable Mycobacterial cells.

The method of the invention also allows detection of Mycobacteria, for example in blood samples, at very early stages of infection, and before any clinical symptoms are visible. The method may be able to identify the presence of live Mycobacteria when they are present in a sample at very low numbers, for example less than 10 cells per sample.

The method of the invention could also be used to monitor the efficacy of a treatment, and to screen for whether the numbers of bacteria are reducing as treatment is given.

Two or more different target Mycobacteria may be identified in a sample at the same time by using a broad host range bacteriophage or by using two or more bacteriophages that specifically infect the two or more different target Mycobacteria. Signature sequences from the two or more different Mycobacteria may be identified by any method capable of identifying a specific DNA sequence, for example using PCR reactions with primers specific to each target *Mycobacterium*. This allows two or more different target Mycobacteria to be identified in a sample at the same time.

In another aspect the present invention provides the use of a bacteriophage that specifically infects a target mycobacterial species in a method for detecting infection by the target *Mycobacterium* wherein the bacteriophage lyses the target *Mycobacterium* to release mycobacterial DNA and signature mycobacterial DNA sequences are identified by PCR or other method capable of identifying a specific DNA sequence.

In another aspect the present invention provides a kit suitable for performing the method of the present invention.

A kit may comprise a bacteriophage that is specific to a target *mycobacterium* and instructions for their use according to the method of the present invention.

The kit may comprise a substrate that specifically binds to *Mycobacterium*, and in particular to the target *Mycobacterium*.

The kit may further comprise oligonucleotides that allow the specific amplification of a signature DNA sequence in the target *Mycobacterium*.

Figure 2:
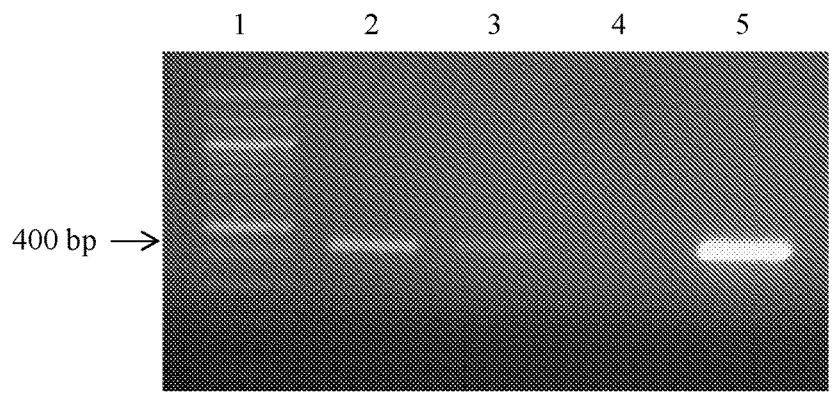
Figure 3:
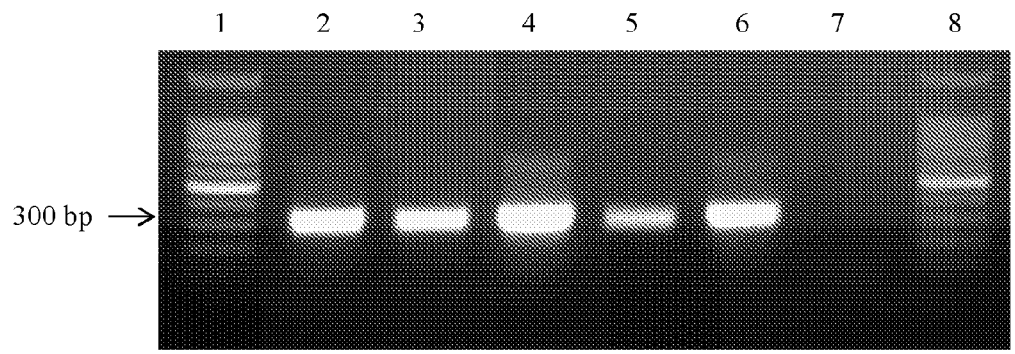
Figure 4:
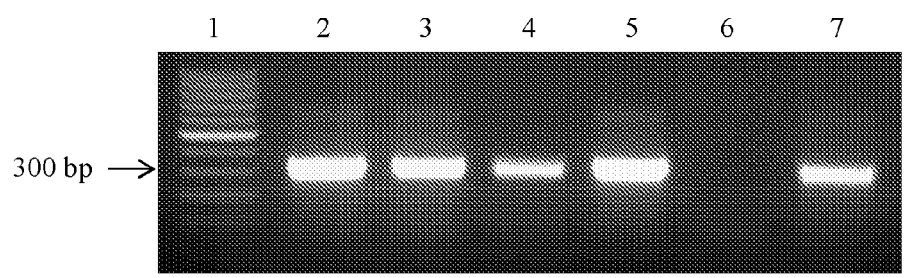
Figure 5:
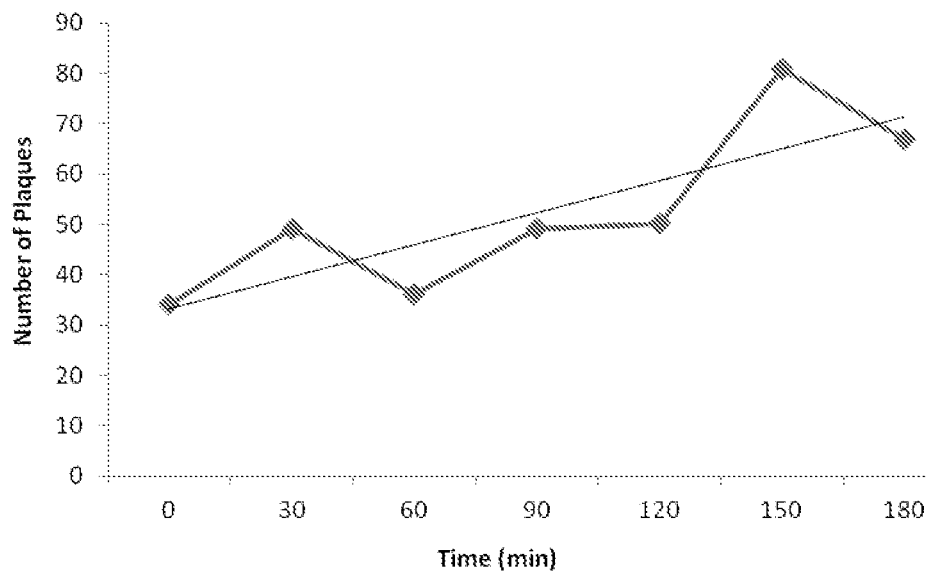
Figure 6:
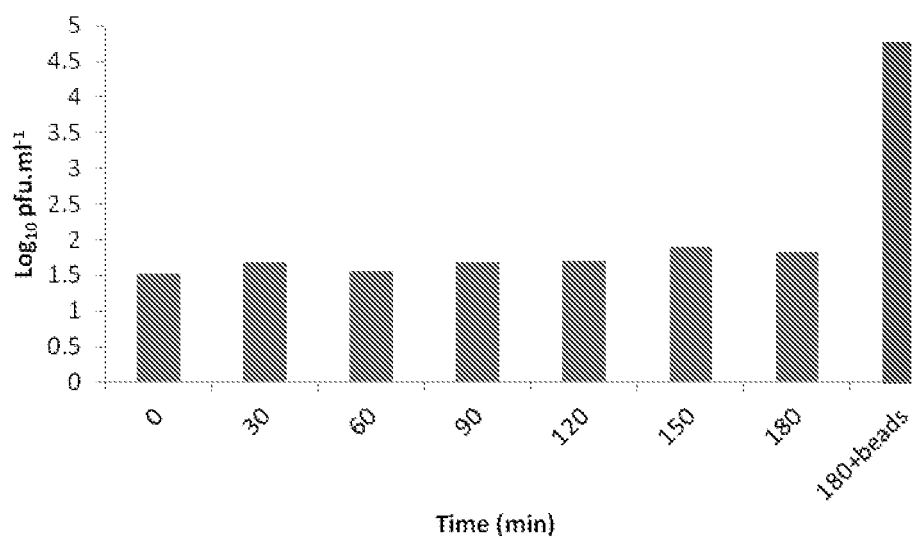
Figure 7:
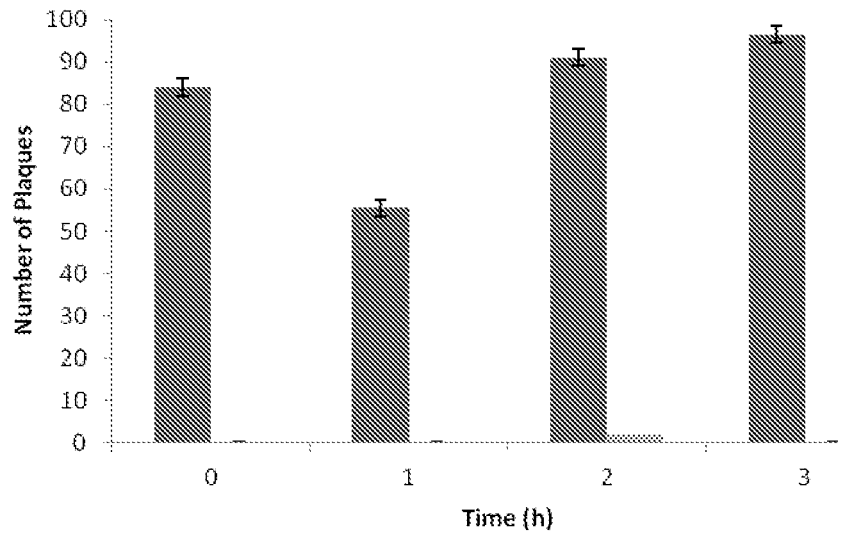
Figure 8:
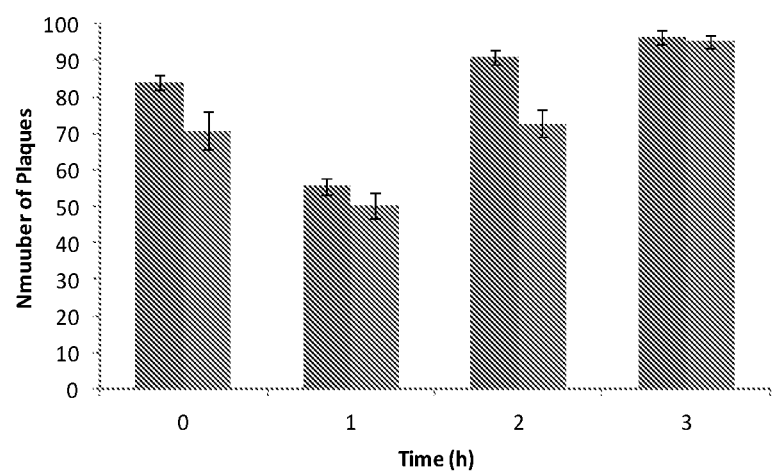
Figure 9:
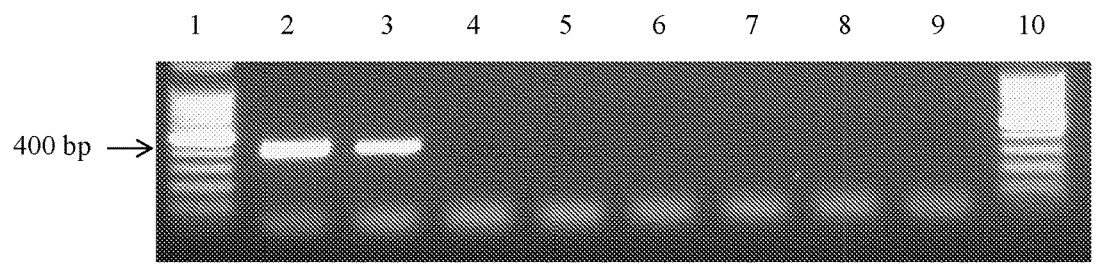
Figure 10:
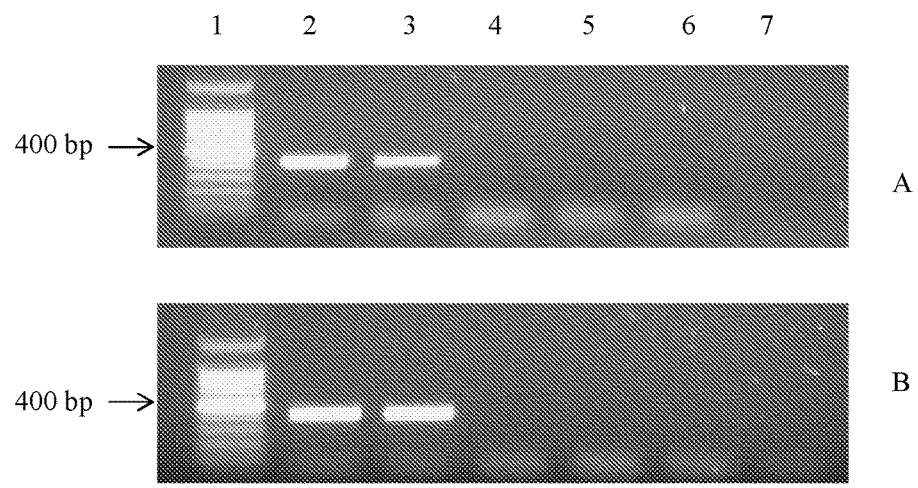
Figure 12:
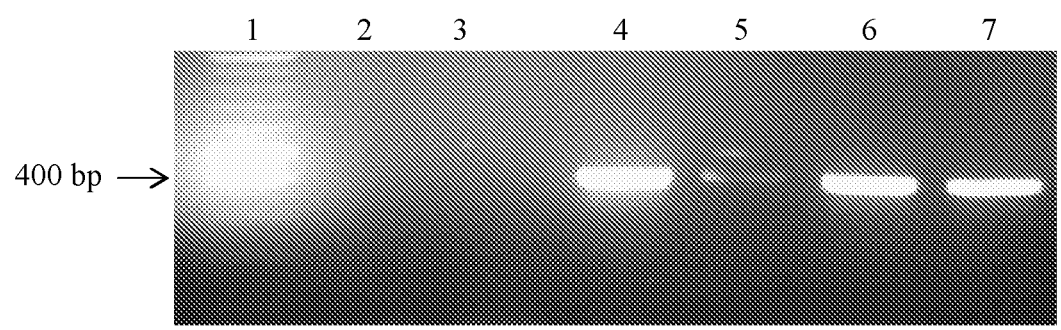
Figure 13:
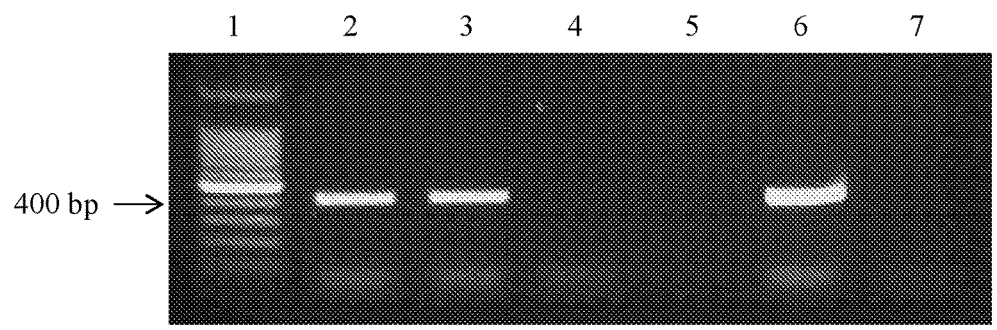
Figure 14:
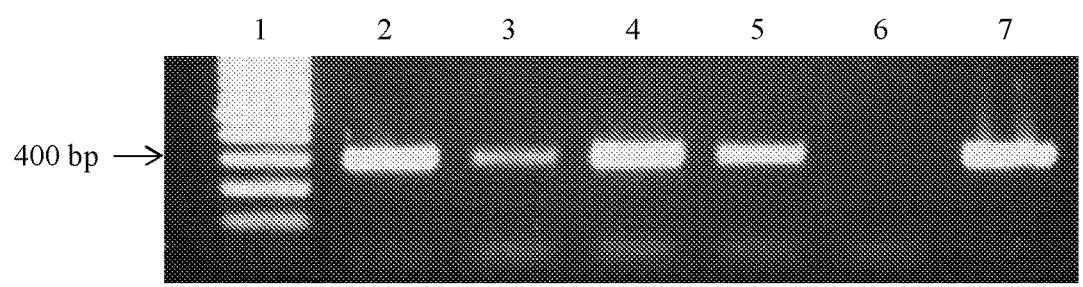
Figure 15:
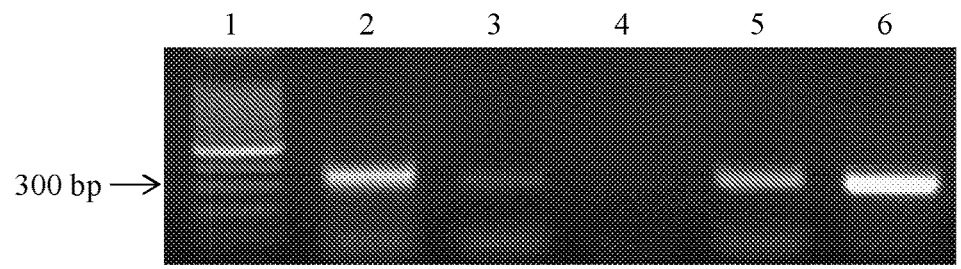
Figure 16:
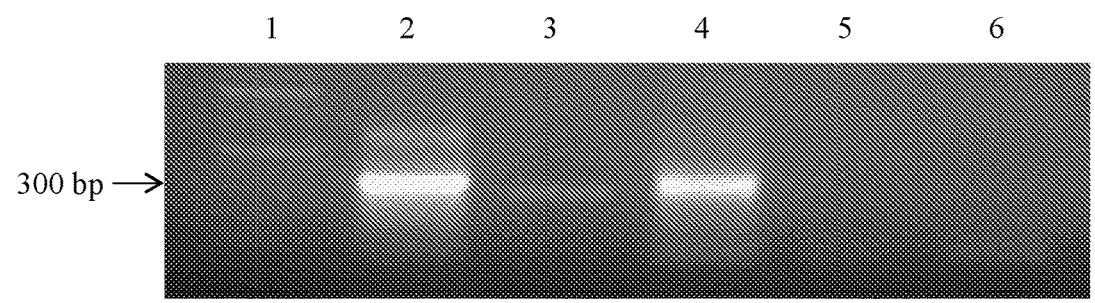
Figure 17:
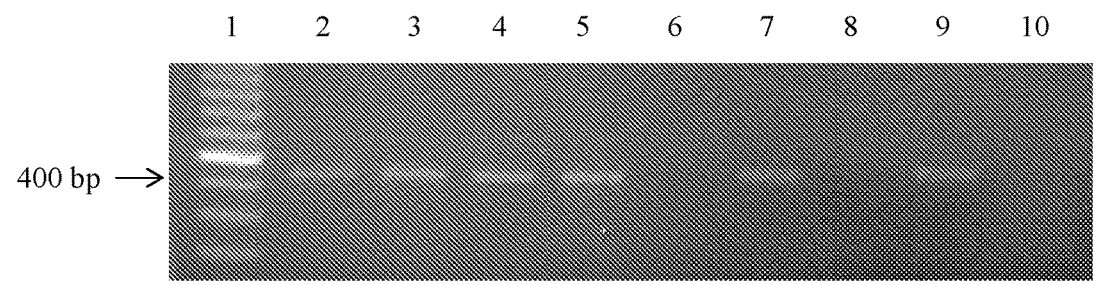
Figure 18:
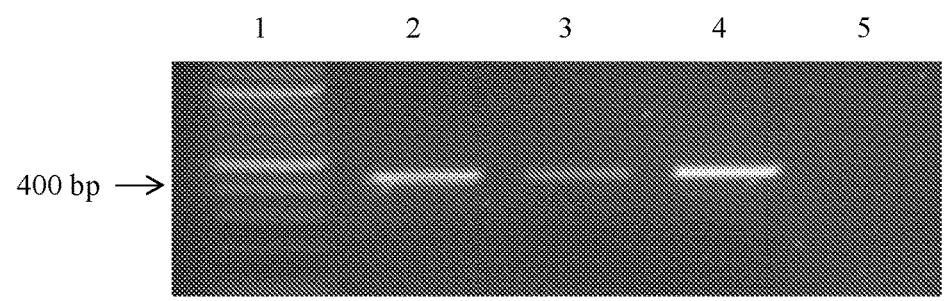

There now follows by way of example only a detailed description of the present invention with reference to the accompanying drawings, in which;

FIG. 1 shows a graph showing the time taken for bacteriophage to be released from *M. smegmatis* (squares) and MAP (diamonds) after 40 min initial incubation to allow phage adsorption. Error bars represent the standard deviations of the mean of number of plaques recovered from the phage assay (n=4);

FIG. 2 shows PCR amplification of the 400 bp F57 DNA region specific for MAP. Lane 1, 100 bp DNA ladder. Lane 2, template DNA removed from bacteriophage-lysed MAP cells. Lane 3, template from non-bacteriophage-lysed MAP cells. Lane 4, negative control (Sterile Distilled Water). Lane 5, positive control (genomic MAP K10 DNA);

FIG. 3 shows a gel showing the effect of removing potential DNA carry-over contamination from the pure cultures on the bacteriophage one day assay. PCR amplification of the approximate 300 bp IS900 DNA region specific to MAP. Lane 1 and 8, 100 bp DNA ladder. Lane 2 and 4, template DNA removed from bacteriophage-lysed MAP cells (strains K10 and ATCC 19851, respectively). Lane 3 and 5, template from non-bacteriophage lysed MAP cells (K10 and ATCC 19851, respectively). Lane 6, positive control (genomic MAP K10 DNA). Lane 7, negative control (SDW);

FIG. 4 shows a gel showing PCR amplification of the approximate 300 bp IS900 DNA region specific to MAP. Lane 1, 100 bp DNA ladder. Lane 2 to 5, template MAP DNA amplified from non-bacteriophage lysed MAP cells (K10) diluted from $1\times10^6$ to $1\times10^3$ pfu.ml$^{-1}$. Lane 6, negative control (SDW). Lane 7, positive control (genomic MAP K10 DNA);

FIG. 5 shows detection of dissociated MAP cells in the supernatant during 3 h incubation on magnetic beads; the graph shows the number of plaques formed by bacteriophages recovered from the supernatant during PMMS every 15 minutes for 3 h. The trend-line represents the general increase over time in the number of MAP cells dissociating from the beads detected by the FPTB assay;

FIG. 6 shows the number of MAP cells dissociated from the magnetic beads during incubation at 37° C. The graph shows the plaque numbers recovered from the supernatant during PMMS every 15 minutes for 3 h (blue bars) and from the beads after 3 h of incubation (right hand bar);

FIG. 7 shows MAP cell dissociation in PBS compared to Media Plus (MP). The graph shows the number plaques recovered every hour from the supernatant of MAP cells isolated and suspended in either MP (left hand bar of each pair) or PBS (right hand bar of each pair). Unpaired T-test was used to determine significance of difference between MAP detection in PBS and MP. Error bars represent the standard deviations of the mean of number of plaques recovered from the phage assay (n=3);

FIG. 8 shows MAP cell dissociation in MP at pH 7.4 compared to 6.6. The graph shows the number plaques recovered every hour from the supernatant of MAP cells isolated and suspended in either MP (red bars) or PBS (green bars). Unpaired T-test was used to determine significance of difference between MAP detection in PBS and MP. Error bars represent the standard deviations of the mean of number of plaques recovered from the phage assay (n=3);

FIG. 9 shows results of an experiment to determine the lowest possible denaturing temperature able to amplify genomic MAP DNA but not lyse MAP cells (a) PCR amplification of the 400 bp F57 DNA region specific for MAP. Lane 1 and 10, 100 bp DNA ladder. Lanes 2, 4, 6 and 8 contain genomic MAP (K10) DNA. Lanes 3, 5, 7 and 9 contain whole MAP cells (K10). Lanes 2 & 3, 4 & 5, 6 & 7 and 8 & 9 had a denaturing temperature of 94, 85.1, 74.8 and 70° C., respectively;

FIG. 10 shows results of an experiment for determining the lowest possible denaturing temperature able to amplify genomic MAP DNA but not lyse MAP cells (b) PCR amplification of the 400 bp F57 DNA region specific for MAP. Experiments represented in both panels were performed using the same PCR temperature conditions. Panel A shows results gained using genomic MAP DNA (K10) and Panel B shows results gained using MAP cells (K10). Lane 1, 100 bp DNA ladder. Lanes 2 to 6 used a denaturing temperature of 95, 92.6, 89.6, 83.1 and 80° C., respectively. Lane 7 was the negative control (SDW);

FIG. 11 shows SEQ ID NO. 1—the IS900 signature sequence specific to MAP cells;

FIG. 12 shows results of an experiment using spin columns to prevent detection of uninfected MAP cells by the PCR assay. PCR amplification of the 400 bp F57 DNA region specific for MAP. Lane 1, 100 bp DNA ladder. Lane 2, template DNA removed from bacteriophage-lysed MAP cells. Lane 3, template from non-bacteriophage-lysed MAP cells. Lane 4, concentrated template DNA removed from bacteriophage-lysed MAP cells. Lane 5, concentrated template from non-bacteriophage-lysed MAP cells. Lane 6, positive control (genomic MAP K10 DNA). Lane 7, negative control (SDW);

FIG. 13 shows results of an experiment testing use of spin columns to separate uninfected MAP cells from free DNA. PCR amplification of the 400 bp F57 DNA region specific for MAP. Lane 1, 100 bp DNA ladder. Lane 2, concentrated template DNA removed from bacteriophage-lysed MAP cells. Lane 3, concentrated template DNA removed from non-bacteriophage infected MAP cells. Lane 4, concentrated template DNA removed from bacteriophage infected *M. smegmatis* cells. Lane 5, concentrated template from non-bacteriophage lysed *M. smegmatis* cells. Lane 6, positive control (genomic MAP K10 DNA). Lane 7, negative control (SDW);

FIG. 14 shows results of an experiment testing use of spin columns to separate uninfected MAP cells from free DNA after two rounds of PMMS. PCR amplification of the 400 bp F57 DNA region specific for MAP. Lane 1, 100 bp DNA ladder. Lane 2, concentrated template DNA removed from bacteriophage-lysed MAP cells. Lane 3, concentrated template DNA removed from non-bacteriophage infected MAP cells after one round of PMMS. Lane 4, concentrated template DNA removed from bacteriophage infected MAP cells after two rounds of PMMS. Lane 5, concentrated template from non-bacteriophage infected MAP cells after two rounds of PMMS Lane 6, negative control (SDW). Lane 7, positive control (genomic MAP K10 DNA);

FIG. 15 shows results of an experiment testing the effect of spin column buffer on the release of MAP DNA. PCR amplification of the approximate 300 bp IS900 DNA region specific to MAP. Lane 1, 100 bp DNA ladder. Lane 2 to 5, MAP cells (K10) diluted from $1 \times 10^4$ pfu.ml$^{-1}$ to $1 \times 10^1$ pfu.ml$^{-1}$. Lane 6, positive control (genomic MAP K10 DNA);

FIG. 16 shows results of an experiment testing MAP DNA detection after one and two rounds of PMMS without spin column concentration. PCR amplification of the approximate 300 bp IS900 DNA region specific to MAP. Lane 1, 100 bp DNA ladder. Lanes 2 and 3 used template DNA after one round of PMMS. Lanes 4 and 5 used template DNA after two rounds of PMMS. Lanes 2 and 4 were phage infected MAP cells (K10) Lanes 3 and 5 were uninfected MAP cells. Lane 6 was negative control (SDW);

FIG. 17 shows MAP K10 and B4 DNA detection after one and two rounds of PMMS without spin column concentration. PCR amplification of the 400 bp F57 DNA region specific for MAP. Lane 1, 100 bp DNA ladder. Lanes 2 to 5, one round of PMMS; Lanes 6 to 9, two rounds of PMMS. Lanes 2, 3, 6 and 7 were strain K10. Lanes 4, 5, 8 and 9 were strains B4. Phage were added to samples in lanes 3, 5, 7 and 9. Lane 10 was negative control (SDW);

FIG. 18 shows MAP ATCC 19851 DNA detection after two rounds of PMMS without spin column concentration. PCR amplification of the 400 bp F57 DNA region specific for MAP. Lane 1, 100 bp DNA ladder. Lane 2, MAP (ATCC 19851) infected with bacteriophage. Lane 3, MAP not infected with bacteriophage. Lane 4, positive control (genomic MAP K10 DNA). Lane 5, negative control (SDW).

Figures 19, 20:
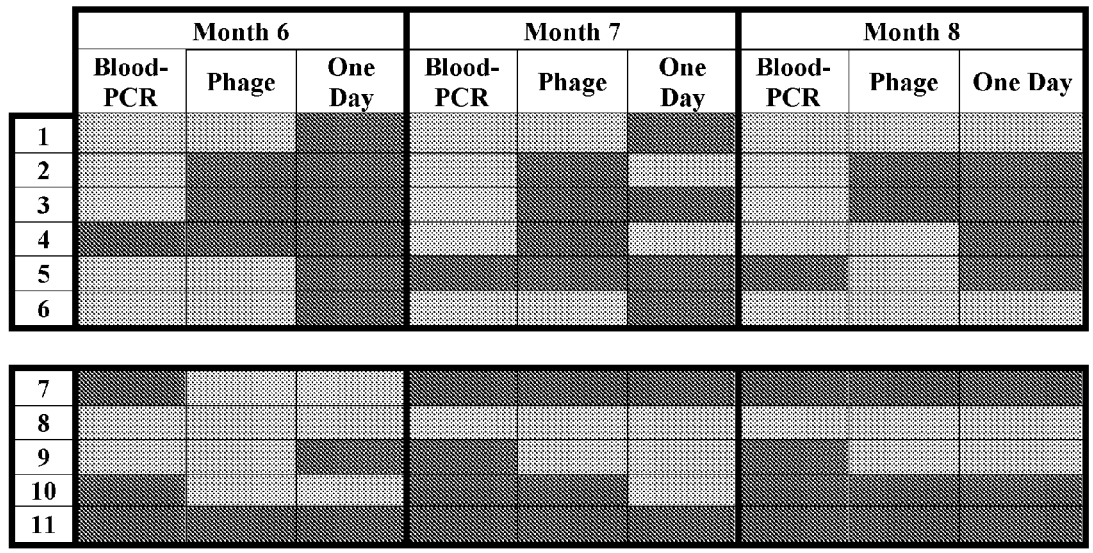
Figure 21:
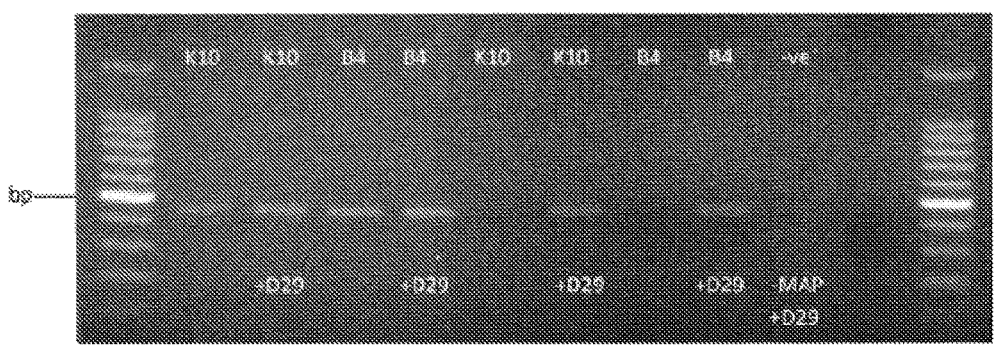

FIG. 19 shows ability of the One Day assay to detect MAP early in the blood of experimentally infected herds compared to direct blood-PCR and the blood phage assay. Light grey—denotes no MAP was detected from either blood-PCR or phage assay. Dark grey—denotes that MAP was detected from either the blood-PCR or phage assay;

FIG. 20 shows a table of correlations between the one day assay with the phage assay and the blood PCR test; and FIG. 21 shows a gel showing results of assay. Two strains of MAP were tested, namely K10 and B4. Lanes 1-4, one round of PMMS; Lanes 5-8, two rounds of PMMS. Phage were added to samples in lanes 2, 4, 6, 8 and 9. No MAP cells were added to sample in lane 9 (negative control)

RESULTS

Determining the Time Taken for Bacteriophage D29 to Release DNA from MAP

To be able to detect the DNA from MAP lysed by the bacteriophage, specific knowledge of the life cycle of phage D29 is required. When using the phage to release the DNA from cells in a sample as a template for PCR, if the sample is taken too early before the cells are lysed, no DNA will be detected. If the sample is left too long after lysis, the DNA may have started to degrade by nucleases released from the lysed MAP cells and again this would lead to loss of signal. Therefore being able to determine exactly when the cells are lysed by the phage under the experimental conditions to be used will enable good template DNA to be recovered for detection by PCR.

Standard protocols exist to measure bacteriophage growth and replication within a host. Generally speaking, without the use of a phagecidal agent, the effect of different numbers of phage on host cells, burst size and the measurement of the eclipse phase has to be carried out by a series of dilutions. To measure the eclipse phase of the phage, both host and phage would normally be diluted to a countable and detectable range, which is time consuming and requires a lot of dilution and sampling. To simplify this experiment FAS was used to inactivate the bacteriophage after allowing just a short time for infection, so that the eclipse phase of D29 could be more easily determined.

FIG. 1 shows that using this method, the eclipse phase of D29 when infecting *M. smegmatis* was found to be around 90 min. However when the same method was used to determine the eclipse phase for phage D29 infecting MAP, the eclipse phase was found to be longer at 120 min. Therefore it was determined that if using these phage as a lysing agent to detect MAP, samples should be left for at least 160 min after infection.

Isolating *Mycobacterium avium* subsp. *paratuberculosis* and Extracting DNA Using Bacteriophage aMP3 and aMptD, that bind specifically to MAP, were coupled to magnetic beads to facilitate MAP cell capture. To develop a one tube assay, these were used to capture and hold the MAP cells before adding the phage to achieve cell lysis of viable cells.

The PMMS method was used initially to isolate MAP cells (enumerated using the phage assay as $1\times10^4$ pfu.ml$^{-1}$) from FPTB Media Plus (MP). After PMMS one sample was inoculated with bacteriophage (100 µl of reconstituted FPTB bacteriophage) and one sample was incubated with 100 µl MP alone. Each sample of MAP was then incubated at 37° C. to for 180 min, as was determined to be the optimal time to allow adsorption, replication and lysis of the MAP cells by the bacteriophage in the previous experiment. After incubation, the cells were centrifuged (10 s pulse at 13,000× g) to collect beads and any unlysed MAP cells still attached to them at the bottom of the tube, and the samples were then placed onto a PMMS magnet holder.

MAP genomic DNA released by the phage should be present in the supernatant. In this case F57 PCR amplification was carried out to determine whether released MAP DNA could be detected.

The results (FIG. 2, lane 2) show that when the phage were added to the sample a strong band was produced at the expected size of approximately 400 bp. However in the negative control, where the phage were not added to lyse the cells, a faint PCR product was visible (FIG. 2, lane 3). This suggested that there was free MAP DNA in the control sample, or that some contamination of the sample with bacteriophage had occurred or that intact MAP cells that had not been lysed by the phage may have been released into the supernatant and acted as template DNA for the PCR reaction if they had been lysed during the heating (denaturation) step of the PCR. This can be eliminated by optimising the reaction conditions.

Optimising Bacteriophage Mediated Cell Lysis PCR-detection

Removing Possible Free MAP DNA

Bacterial laboratory cultures can have free DNA in them following autolysis of old or dying cells and this may have resulted in the positive PCR amplification result. Before repeating the experiment described above, cultures of MAP strain K10 and ATCC 19851 were subjected to DNase I (NEB, UK) treatment. The aim was to degrade any free genomic DNA that may have been carried from the cultures into the samples. The washing step used during PMMS would remove the DNase I from the sample so that any template DNA released after this could still be detected. In this experiment the IS900 P90 PCR was used to increase the sensitivity of the detection event and to reduce the impact of any low levels of DNase I remaining in the samples. The results (FIG. 3) show that once again a stronger PCR product (IS900 PCR product =approx. 300 bp) was amplified when the bacteriophage was used to release the MAP DNA from the strains K10 and ATCC 19851, however a strong PCR band was still seen in the controls without bacteriophage added to them (FIG. 3, lanes 3 and 5). This showed that the DNase I was not having an adverse effect on the PCR and if there was free DNA in the original sample it would have been removed. However this treatment did not remove the appearance of PCR products in the negative control samples and suggests that this false positive result was either due to bacteriophage contamination or free cells are released into the supernatant being detected.

Removing Possible Bacteriophage Contamination

To rule out bacteriophage contamination, the experiment above was repeated using fresh pipettes, pipette tips on a new bench that had not been used with mycobacteriophage. New reagents and equipment was also used. Four samples of MAP cells (K10) containing from $1\times10^6$ to $1\times10^3$ pfu.ml$^{-1}$ were used. The IS900 PCR was used again to make sure any DNA that may have been present in the sample was detected. The results (FIG. 4) show that when no bacteriophage were added, strong PCR signals were still detected in each of the cell suspension tested. This suggested that the bacteriophage were not inadvertently introduced into the negative control samples and therefore that the false-positive results may be due to free cells in the sample.

Improving Peptide-mediated Magnetic Capture Efficiency

Bacteriophage contamination and DNA carry over from the pure cultures were ruled out as not being responsible for the strong bands on the uninfected control. Thus the capture efficiency and stability of the cells on the bead surface was investigated. The FPTB assay was used to determine whether MAP cells may be dissociated from the magnetic beads during PMMS. The original protocol when using PMMS only required MAP cell capture for 30 min, and subsequent washing would only take an extra 20 min. Thus MAP cells would only be required to remain on the magnetic beads for a maximum of 1 h. During the one day assay, the cells are required to remain on the beads for almost 4 h, which may give the cells enough time to begin dissociating from the peptides binding them. Therefore an experiment was designed to determine the number of cells that could be detected from the beads during the 3 h incubation required.

To do this approximately $1\times10^6$ pfu.ml$^{-1}$ of MAP cells (K10) were mixed with the magnetic beads for 15 min and PMMS was carried out. The samples were placed at 37° C. and the samples were placed on magnetic racks and 100 µl was taken from the supernatant at 30 min intervals for 3 h. The FPTB assay was carried out to detect any cells released into the supernatant. The results showed that as the time went on the number of cells detected in the supernatant almost doubled from time point zero to time point 180. There was a peak at 150 min, where $8.1\times10^2$ pfu.ml$^{-1}$ were detected, however this fell to $6.7\times10^2$ pfu.ml after 180 min (FIG. 5). The results also show however that there was $6\times10^5$ pfu.ml$^{-1}$ detectable cells attached to the beads which was less than half a $\log_{10}$ lower pfu.ml$^{-1}$ compared to the initial inoculum and almost 4 $\log_{10}$ higher the numbers of cells that had dissociated from the beads (FIG. 6) suggesting that the majority of the cells remained attached to the beads.

The results from this experiment show that MAP can fall of the beads, and may be detectable by PCR once in the supernatant. Several parameters such as pH, temperature and length of time, can be altered that can increase or decrease the rate of dissociation of any reversible binding event. In this case the length of incubation is difficult to change as the bacteriophage require certain amount of time to release the host cell's DNA. Shortening the incubation time may result in cells not lysing efficiently and increasing the incubation time may result in more MAP cells dissociating from the beads creating further problems.

Hence it was decided that changing the pH a parameter that could be used to optimise cell binding to the beads. The original PMMS methods used PBS (pH 7.4) to bind the MAP cells to the beads. In the modified protocol developed for the MAP blood assay, MP was used instead which has a pH of 6.6. This shift in pH may alter the association binding constants which may in turn have resulted in the dissociation of the MAP cells into the supernatant. To investigate the effect of pH, the experiment described above was repeated, however this time cells were suspended in PBS or MP and every hour samples were tested using the FPTB assay to compare the dissociation rate of the MAP cells incubated in the two solutions. The results show that when PBS was used there was significantly lower detection ($P<0.001$) of MAP cells in the supernatant at each time point, compared to the similar number of MAP cells detected Since the pH of MP (6.6) was lower than PBS (7.4), the pH of MP was adjusted using Sodium Hydroxide. The experiment above was repeated however the results show that there was no significant difference between the number of MAP cells detected either MP at pH 7.4 or 6.6 (FIG. 7). At this point an alternative explanation was proposed for the original result, in that the lack of MAP dissociation detected in the PBS sample may have been due to the PBS inhibiting phage binding, and thereby detection of MSP cells.

So the experiment was repeated, however the number of MAP cells detected on the beads was also determined using the FPTB assay as well as monitoring the number of MAP cells in the supernatant. The results (FIG. 8) show that when the beads were tested, no MAP was detected suggesting that PBS does not allow phage to infect well and therefore the original conclusion that the difference in pH affected the rate of dissociation may not have been true.

As the effect of pH was not determined to have a major affect on reducing the dissociation constant of the MAP on the magnetic beads, temperature was instead investigated as an alternative parameter that could be altered. The temperature (37° C.) was originally chosen as it has been optimised in the FPTB assay to allow good growth and replication of the bacteriophage as well as the fast growing *M. smegmatis*. It is also known that the temperature can affect the time taken for D29 phage release in Mycobacteria. Thus reducing the temperature may decrease the number of cells dissociating from the beads, but may increase the amount of time needed for the phage to lyse their host.

When trying to assess this using the phage assay at a lower temperature, good *M. smegmatis* lawns did not form, which resulted in difficulty in visualising the plaques. Hence a different approach to determine when the DNA was released from the cells at lower temperatures was used. Commercial kits that determine when cell integrity is compromised are marketed. The CellTox Green Cytoxicity Assay (Promega, UK) contains a dye that binds to DNA of cells with impaired membrane integrity. Thus, when a cell is lysed open by the phage, there should be an increase in signal as DNA is released which in turn could be used to determine the end of the eclipse phase. By detecting when the host cell DNA was released would allow the timing of sampling for PCR detection of this DNA to be optimally timed.

The cytoxicity assay was carried out on MAP and *M. smegmatis*. As controls, a sample containing just phage and a sample consisting of just MP (no cells phage or bacteria present) were used. The MAP and *M. smegmatis* samples (containing $1\times10^5$ pfu.ml$^{-1}$ of cells) were infected with bacteriophage D29 at an MOT of 10. The same amount of phage was added to bacteria free sample and nothing was added to the negative MP alone control. Each sample was incubated for 40 min to allow phage infection and then plated on black 96-well plates and incubated for 4 h, with a fluorescence reading taken every 10 min. The results show that fluorescence steadily decreased as time went on from each of the samples. The media alone negative control indicated the background level of fluorescence was lower than each of the other samples, suggesting DNA was detected either from within the phage or the cells. However a lysis event during the 4 h of incubation was not detected.

Although from this result the lower temperature did not seem to even induce bacteriophage-mediated lysis of the host cells, there may have been drawbacks using the commercial cytoxocity assay for this experiment, as it was not originally designed to be used in this way. Although the binding of the cells was thought to be the reason for the false-positive results gained using uninfected cells, no conclusive proof could be gained to show this was the case from these experiments and changing the binding conditions to try and optimise cell binding proved to be difficult as it interfered with the efficiency of the phage lysis steps.

Preventing Detection of Unlysed MAP Cells

Unlysed dissociated MAP cells may have been detected by the PCR assay since the initial 95° C. denaturing step can lyse open bacterial cells (as used when performing direct colony PCR). This lysis however was not desirable and the result was a false-positive PCR result in our assay. The denaturing temperature was therefore reduced to try and reduce cell lysis. Genomic MAP DNA (K10) and $10^2$ pfu.ml$^{-1}$ of MAP cells (K10) were prepared as 10 µl template DNA in 25 µl PCR reaction volumes. The MAP cells were initially washed twice by centrifugation and resuspension in fresh MP before being used as template. A non-Hot Start PCR master mix (Qiagen) was used in the reaction. A temperature gradient PCR was used to change the denaturing temperature to 94, 85.1, 74.8 and 70° C. Genomic DNA was used to ensure the PCR was still able to amplify the correct PCR products, and this was compared to the ability of the PCR to lyse open and amplify DNA from whole cells. The results show that only the genomic MAP and the MAP cells at 94° C. yielded a good PCR product after the MAP-specific F57 PCR (FIG. 9). The experiment was repeated but a smaller range of temperatures was used for denaturing: 95, 92.6, 89.6, 83.1 and 80° C. The again results showed that the PCR products were only amplified when the denaturation temperatures of 95 and 92.6° C. were used, showing that the free genomic DNA could not be amplified in preference to that from whole cells by simply reducing the denaturing temperature (FIG. 10b).

The next step in trying to prevent the PCR detection of the uninfected control was to remove the dissociated MAP cells from the sample. When performing the PCR identification step during a blood assay which used plaque assays, spin columns are used to isolate and concentrate DNA from plaque samples. Spin columns may act as a barrier to the free cells in the supernatant whilst still binding and concentrating the free DNA that would be released from the cells after phage infection.

To test whether this approach would work, MAP cells K10 ($1\times10^4$ pfu.ml$^{-1}$) were processed through the PMMS protocol. The cells were suspended in 1 ml of MP and incubated for 3 h at 37° C. with or without bacteriophage. After incubation 10 µl was removed from the supernatant of each sample and the rest was processed through the DNA concentrator spin column. The eluted DNA and the non-concentrated sample was then tested for the presence of detectable MAP DNA using the MAP-specific F57 PCR. The results show that neither of the unconcentrated samples gave a positive PCR result. The concentrated, bacteriophage-infected sample produced a very strong PCR amplification, however the phage uninfected control sample also resulted in the amplification of the MAP-specific band, although the amplification was weaker indicated that lower amounts of DNA were present. However, the negative PCR control sample (no DNA template added) also produced a strong band, which suggested that a contamination error (FIG. 12).

Due to this problem the experiment was repeated, using M. smegmatis as well as SDW as negative experimental and PCR controls. The results show that, as expected, M. smegmatis and the no DNA (SDW) negative controls did not produce positive PCR results. However both the infected and uninfected MAP samples gave strong positive PCR bands, even after separating the sample using the spin columns (FIG. 13).

Both infected and uninfected samples once again yielded positive bands, suggesting the whole cells may still be being detected. As it is known that the MAP cells can dissociate from the beads during the 3 h incubation, using the beads again after cell lysis to remove any free cells was investigated. The experiment was repeated, however when the cells were suspended in 1 ml of MP, and the beads removed (by pulse centrifugation and magnetic separation) the supernatant was removed and mixed with fresh magnetic beads. The samples were then incubated by rotating for 30 min to allow any free MAP cells to bind to the beads. The samples were then placed back on the magnetic rack and the supernatant was then removed processed through the spin columns and the PCR detection assay carried out again.

The results show that after the first round of PMMS there was a stronger PCR amplification from the phage-infected sample compared to the uninfected sample. However after the second round there was still a strong, although fainter, PCR band from the uninfected sample (FIG. 14).

There were strong PCR products amplified once again from the uninfected MAP cells even after two rounds of PMMS. The DNA concentrator uses a DNA binding buffer which may induce lysis of the bacterial cells. Although the components of the kit are unavailable, the hypothesis that the buffer may induce cell lysis was investigated. MAP cells (K10) were 10-fold serially diluted from $1\times10^4$ pfu.ml$^{-1}$ to $1\times10^1$ pfu.ml$^{-1}$ and were treated as supernatant after PMMS therefore the samples were subjected to DNA concentration using the spin columns and the eluted template amplified using MAP-specific IS900 PCR. The results show that apart from being unable detect DNA from the $10^2$ pfu.ml$^{-1}$ sample, DNA was detected from each of the other concentrations of cells tested (FIG. 16). It had shown therefore that the buffers in the DNA concentrator kit, has the ability to break open MAP cells and release their DNA, which may explain why positive bands were still being detected from samples not infected with bacteriophage.

The experiment with two rounds of PMMS was repeated using $1\times10^4$ pfu.ml$^{-1}$ of MAP cells (K10) but this time the spin-columns were not used to concentrate the DNA. When the PMMS was carried out the beads were finally resuspended in 100 µl of MP. The sample was then pulse centrifuged and placed and magnetic rack. A 10 µl sample of the supernatant was taken as template DNA and the rest was placed in a fresh microcentrifuge tube. The sample was mixed with fresh magnetic beads and incubated whilst rotating for 30 min. The beads were separated on a magnetic rack and 10 µl of the supernatant was used as template DNA. The MAP-specific IS900 PCR was then carried out. The results show that MAP was detected strongly when bacteriophage was used in both the first and second round of PMMS. However only a faint PCR products was amplified in the uninfected sample after the first round of PMMS and no amplification was seen at all after the second round of PMMS (FIG. 16).

The experiment with two rounds of beads was repeated using $1\times10^4$ pfu.ml$^{-1}$ of MAP strains K10 and a different MAP strain; B4. The less sensitive MAP-specific F57 PCR assay was also used. The results show that once again after the first round of PMMS, PCR products were amplified from each of the samples. After the second round of PMMS, only the MAP samples infected with bacteriophage were detected, the uninfected were not (FIG. 17). The experiment was repeated with MAP strain ATCC 19851. However in this case the results show that the MAP DNA was detected from the uninfected samples after the second round of PMMS (FIG. 18).

Evaluating the Preliminary Assay Design on Blood Samples from Experimentally Infected Calves.

Although not fully optimised, the samples from animals were tested using the preliminary assay design described above. Surplus blood from the samples was subjected to PMMS and then resuspended in 100 µl of MP. The beads were separated from the samples by pulse centrifugation and resting on a magnet. The supernatant was placed into a new microcentrifuge tube and fresh magnetic beads were added. The samples were incubated for 30 min rotating at room temperature. The beads were separated by pulse centrifuging and resting the samples on a magnet. Ten microliter samples were then used as template DNA for MAP specific IS900 PCR. FIG. 19 shows the results of the one day assay compared to the original blood PCR's and the blood phage assay.

In month 6, the one day assay detected MAP DNA in eight animals (numbers 1-6, 9 and 11). Viable MAP was detected in four animals in month 6; 4, 7, 10 and 11, all of which agreed with the one day assay. The direct blood PCR detected MAP DNA in four animals; 4, 7, 10 and 11, which only agreed with two samples from the one day assay.

In month 7, six animals; 1, 3, 5, 6, 7 and 11 were positive from the one day, which agreed with four of the seven positive results for the detection of viable MAP and three of the five positive results for the direct blood PCR. In month 8, the one day assay detected MAP in seven animals; 2-5, 7, 10 and 11. This agreed with all five of the positive samples from the phage assay and four out of the five positive for the direct blood-PCR.

Conclusion

Whilst some further refinements to the assay may be required it is clear to the skilled man from the data present here that the method subject of this application does work and has utility in the field.

Discussion

The aim of the invention and experiments presented here is to develop a novel robust method for detecting and enumerating viable MAP, preferably within one day, in a format that can be automated. There is commercially available equipment that allows the separation and washing of cells using bead capture technology (Tecan Group; Te-MgS, Life Technologies; Dynabead Tech). As long as the technology was kept within a one-tube format, automation would be possible. Capturing and detecting bacteria has been carried out before, for example on E. coli, Helicobacter pylori and L. monocytogenes. However the majority of these methods use PCR as an end-point identification which does not differentiate between live and dead cells. It is important to assess the viability status of organisms to determine whether they pose a threat to public health. There are several stains that can be used to determine bacteria viability, however due to the unusual cell wall of Mycobacteria these tests tend to be less efficient. Culture is the ideal method for determining viability, however with Mycobacteria such as MAP, it can take several weeks for colonies to develop.

Lytic bacteriophage infect and break open bacteria efficiently within hours. A modification of The FASTPlaqueTB™ (FPTB) assay described in WO 92/02633 was used to determine how long it takes for phage D29, once it had infected the cells, to release progeny phage (eclipse phase) from MAP and *M. smegmatis*. There have been differences in the reported eclipse phase of D29 when infecting different Mycobacteria. When using the FPTB assay the eclipse phase of D29 in *M. smegmatis* was 90 min. In *M. tuberculosis* and *M. avium* however it has been noted that the length of the eclipse phase for D29 is much longer at around 120 min. This corresponds to the 120-135 min eclipse phase found using the FPTB assay when D29 infected MAP cells. Knowing that the latent period was at least 260 min, and incubation time of 3 h was used to allow for good lysis of MAP cells from the samples.

The novelty of the one day assay described herein is that MAP cells can be isolated from a medium (such as blood) on magnetic beads. The beads can then be infected in situ with bacteriophage. Only viable MAP cells will support bacteriophage replication and lyse the host cell to facilitate the release of progeny phage particles, which will also release genomic MAP DNA. The DNA released from the MAP cells can then be detected by PCR. The initial experimental design was to determine whether MAP DNA could be detected from MAP cells exposed to bacteriophage compared to those that were not, as the novelty of the assay is that only viable cells can be detected. The results presented here showed that a faint MAP PCR product was amplified from the uninfected sample, routine optimisation of the method will allow this to be eliminated. To try to remove the faint PCR product pure cultures of MAP were initially treated with DNase I to eliminate the potential effect of DNA carry over from the cultures of MAP, which may have resulted in amplification of MAP-specific DNA product. Even though contaminating DNA that potentially could have been carried over from the pure culture stock was removed, MAP specific DNA was still amplified by the PCR.

Being able to distinguish between viable and non-viable host MAP cells is vitally important for the detection assay. In a clinical case of Johne's disease and other general infections caused my mycobacterial pathogens, the organisms are taken up by macrophages and either the cells are killed or survive and persist within the cells. The assay was re-optimised to prevent the detection the uninfected cells. During PCR, temperatures at 95° C. are used to denature DNA and to, if used, activate hot-start Taq DNA polymerases. Colony PCR's, that do not use the prepared template DNA but instead use intact cells as the source of template DNA use the denaturing step to heat lyse the cells and release DNA from whole cells. Whole cells free in the sample that are not removed may therefore be detectable. The denaturing temperature was reduced to investigate whether this would stop whole cell lysis and detection. MAP specific PCR's were carried out on whole MAP cells and genomic MAP DNA. The results show however that DNA can only be amplified from the genomic MAP DNA at a minimum denaturing temperature of 92.6° C.

Physical barriers were used next to remove the whole cells from the MAP DNA. DNA spin-columns can be used to clean, concentrate and purify DNA from a range of different samples. Zymo DNA-clean and concentrator was originally designed to concentrate DNA from large sample volumes to very small volumes for downstream processes such as PCR or DNA sequencing. A column matrix is used to capture DNA, where it is washed and eluted off into smaller volumes by a shift in down in pH. The physical barrier of the column was used to block free cells in the solution that may be detected by PCR, at the same time capturing and concentrating free DNA released by the bacteriophage in the infected samples. Therefore physical barrier methods or filtration could be used to remove unlysed cells from the MAP DNA.

Blood samples from calves infected with MAP were tested using the method involving two rounds of MAP beads. This was compared to the blood-phage assay to firstly determine whether viable or not viable cells were detected, but to also test the sensitivity of the MAP detection in blood compared to a direct PCR and the blood phage assay. The results showed that as the month's progressed agreement between all the tests increased, except the blood phage assay and the direct blood PCR, where agreement remained the same at 64%. In month 8 the one day assay agreed with the blood phage assay in 82% of test results. Assuming the assays had that same sensitivity, the discrepancies could be attributed to the one day assay detecting non-viable MAP that may be present in the blood as the one day assay was not fully optimised at the time of the experiment.

When developing the phage-based blood detection method, peptide-mediated magnetic separation (PMMS) was used to concentrate MAP cells and separate them from a potentially inhibitory matrix, before further downstream processes were carried out. PMMS allowed MAP cells to be resuspended in a medium that enables bacteriophage infection of the cells to take place and therefore could be replaced with any separation technique.

PMMS was used to isolate MAP cells from blood. The concentrated cells were then efficiently lysed using the lytic mycobacteriophage D29. Finally DNA released from the infected cells would then be used to detect MAP using PCR amplification of specific signature sequences.

The novelty of the assay described is the use of bacteriophage as a specific lysing agent to indicate viability (only viable cells are able to support phage replication that results in cell lysis). Once lysed, the identity of the viable mycobacterial cell detected is determined by amplification of signature sequence from the bacterial genome.

The technique produces an overall assay in a small tube format, compatible with automation, that is rapid (test results to species level within one day), sensitive and only detects viable cells. The critical process step identified is a second clean up of the DNA lysates prior to PCR amplification.

The Assay
  MAP cells present in blood from infected animals are recovered from matrix by Peptide-mediated Magnetic Separation (PMMS)
    Peptides with MAP-specific binding capacity are coated onto magnetic beads, and are added to blood sample and mixed for 30 min with diluted blood samples.

Beads are recovered using a magnetic rack, and then washed twice before finally resuspended in 100 III of detection media (1 hour total time)

Phage (D29) are added to the sample and incubated for 2 h to allow lysis of infected cells Unlysed (non-viable) cells are then removed from liquid phase by magnetic separation Any remaining unlysed cells that may have been released into the liquid phase are removed by a second round of PMMS (3 hours total time)

The lysis mixture (containing the genomic DNA of the lysed, viable cells) is then used as a template for PCR amplification of signature sequences (in example given the f57 sequence). (3 hours total time)

Demonstration of Assay

Two different strains of MAP were used; K10 and B4. MAP cells were recovered by PMMS and transferred into the assay tube. D29 Phage were added as a specific lysing agent to one sample. After 2 h incubation to allow the phage to lyse open the viable cells, unlysed cells were removed from the tube by either one round (lanes 1-4) or two rounds (lanes 5-8) of PMMS. The remaining lysates were used as a template for PCR amplification of the f57 MAP-specific genome sequence.

The presence of an amplified band in either in the presence or absence of the D29 phage following only one round of PMMS (Lanes 1-4) indicates that intact cells remained in the sample; the genomic DNA is detected from unlysed cells which are then lysed during the PCR amplification process.

Following two rounds of PMMS, a band is detected only in the samples where the D29 phage is added, showing that the phage have specifically lysed the viable Myocbacterial cells, releasing the genomic DNA into the liquid phase and allowing PCR amplification of the f57 sequence Conclusion The second round of PMMS helps to ensure complete removal of un-lysed MAP cells Once unlysed cells removed, only MAP cells infected with phage were detected Phage will only lyse viable MAP cells, therefore the assay detects viable MAP cells in one day Total time required for assay from receiving sample=7 h; this could be reduced; and the steps required are compatible with an automated washing system.

The PCR assay used here is a standard manual tube system, but this could clearly be automated or replaced with a non-PCR based DNA amplification system.

Potential Applications of Assay

Novel rapid method for confirming diagnosis of Johne's disease in cattle. Current tests require repeat milk ELISA assays and are known to be unreliable. This assay could replace the ELISA testing for use in herd control programmes.

Detection of other Mycobacteria in Blood

The assay could be used in combination with other IMS/PMMS methods to allow detection of other Mycobacteria that cause systemic disease in cattle (such as *M. bovis*) or in humans (such as *M. tuberculosis*). For such assays to be developed, the genomic signature sequences have already been identified.

Detection of Mycobacteria from other Sample Types.

IMS can be applied to a wide range of samples types or other sample preparation methods could be used prior to recovery and concentration of the mycobacterial cells by magnetic separation. Examples of other clinical specimens that may be of relevance are semen samples from bulls used in herd assurance programmes.

The invention claimed is:

1. A method for testing the presence or absence of viable target Mycobacteria in a reaction mixture comprising the steps of:
   a) providing a reaction mixture;
   b) admixing a bacteriophage with the reaction mixture under conditions suitable to allow the bacteriophage to infect and lyse any viable target mycobacterial cell present in the reaction mixture, wherein step b) occurs in a single reaction vessel;
   c) removing un-lysed cells from the reaction mixture;
   d) analyzing DNA from the lysed Mycobacteria to identify a signature DNA sequence that occurs in the target *Mycobacterium* species, wherein the presence or absence of the signature DNA correlates to the presence or absence of Mycobacteria in the reaction mixture.

2. The method according to claim 1, wherein the target mycobacterial cell is *Mycobacterium avium* subsp. *paratuberculosis* (MAP), *Mycobacterium tuberculosis*, *Mycobacterium leprae* or *Mycobacterium bovis*.

3. The method according to claim 2, wherein the target mycobacterial cell comprises *Mycobacterium avium* subsp. *paratuberculosis* strain K10, or B4.

4. The method according to claim 1, wherein the bacteriophage is a broad host range mycobacteriophage, D29 or TM4.

5. The method according to claim 1, wherein the bacteriophage only lyses live target mycobacterial cells.

6. The method according to claim 1, wherein the DNA is analysed by PCR using forward and/or reverse primers that anneal specifically to a signature DNA sequence that occurs in the target mycobacterial cell.

7. The method according to claim 1, wherein the signature DNA sequence is a sequence having at least 60%, 70%, 80%, 90%, 95%, 98% or 100% identity to SEQ ID NO: 1.

8. The method according to claim 6, wherein the forward primer has the sequence 5'-CAG CGG CTG CTT TAT ATT CC-3' (SEQ ID NO 2) and/or the reverse primer has the sequence 5'-GGC ACG GCT CTT GTT GTA GT-3' (SEQ ID NO 3).

9. The method according to claim 6, wherein the DNA melting step in the PCR is carried out at a temperature that does not lyse mycobacterial cells, preferably at less than 95° C.

10. The method according to claim 1, wherein the reaction mixture comprises a sample from an animal or human suspected of being infected with the target mycobacterial cell.

11. The method according to claim 1, wherein the reaction mixture comprises a sample of blood or tissue.

12. The method according to claim 1, wherein the reaction mixture comprises a sample of a product for human or animal consumption.

13. The method according to claim 1, wherein steps a) to d) of the method can be performed in one reaction vessel.

14. The method according to claim 1, wherein steps a) to d) of the method can be performed within 24 hours.

15. The method according to claim 1, wherein the method does not comprise the use of antibodies for identifying Mycobacteria or identifying mycobacterial infection.

16. The method according to claim 1, wherein signature sequences from two or more different Mycobacteria are identified.

* * * * *

SEQUENCE LISTING

```
<160> NUMBER OF SEQ ID NOS: 3

<210> SEQ ID NO 1
<211> LENGTH: 1451
<212> TYPE: DNA
<213> ORGANISM: Mycobacterium avium
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (724)..(725)
<223> OTHER INFORMATION: n is a, c, g, or t

<400> SEQUENCE: 1
tccttacctt tcttgaaggg tgttcggggc cgtcgcttag gcttcgaatt gcccagggac      60
gtcgggtatg gcnttcatgt ggttgctgtg ttggatggcc gaaggagatt ggccgcccgc     120
ggtcccgcga cgactcgacc gctaattgag agatgcgatt ggatcgctgt gtaaggacac     180
gtcggcgtgg tcgtctgctg ggttgatctg gacaatgacg gttacggagg tggttgtggc     240
acaacctgtc tgggcgggcg tggacgccgg taaggccgac cattactgca tggttattaa     300
cgacgacgcg cagcgattgc tctcgcagcg ggtggccaac gacgaggccg cgctgctgga     360
gttgattgcg gcggtgacga cgttggccga tggaggcgag gtcacgtggg cgatcgacct     420
caacgccggc ggcgccgcgt tgctgatcgc cttgctcatc gctgccgggc agcggctgct     480
ttatattccc gggcgcacgg tccatcacgc cgcgggtagt taccgcggcg aaggcaagac     540
```

```
cgacgccaaa gacgctgcga tcatcgccga tcaggcccgg atgcgccacg acttgcagcc        600
tctgcgcgcc ggcgatgaca tcgcagtcga gctgcgcatc ctgaccagcc gacgttccga        660
tctggtggct gatcggaccc gggcgatcga accgaatgcg cgcccagctg ctggaatact        720
ttcnncgctg gaacgcgcct tcgactacaa caagagccgt gccgcgctga tcctgcttac        780
tggctaccaa actcccgacg cgctgcgcag cgccggtggc gctcgagtag ccgcgttctt        840
gcgtaaacgc aaggcccgca acgccgatcc cgtcgcagcc accgcgctgc aggccgctaa        900
cgcccaacac agcatcgtgc ccggccaaca actggcggcc actgtggtgg cccgcctggc        960
caaggaggtg atggccctcg acaccgaaat cggcgacacc gacgcgatga tcgaggagcg       1020
atttcgccgc caccgccacg ccgaaatcat cctgagcatg cccggattcg gcgtcatcct       1080
gggcgctgag ttcctcgccg ccaccggcgg ggacatggcc gcattcgcct ccgccgaccg       1140
cctcgccggc gtcgccggcc tggcgccggt accacgagat tccggccgca tcagcggaaa       1200
cctcaaacgc ccccgacgct acgaccggcg cctgctgcgc gcctgctacc tgtcggcctt       1260
ggtcagcatc cgcaccgacc cctcctcgcg cacctactac gaccgaaaac gcaccgaagg       1320
aaaacgccac acccaagccg tcctcgccct ggcccgccgc cgcctcaacg tcctgtgggc       1380
catgctgcgc gaccacgctg tctaccaccc cgcaaccact accgcggcgg cttgacaacg       1440
tcattgagaa t                                                            1451

<210> SEQ ID NO 2
<211> LENGTH: 20
<212> TYPE: DNA
<213> ORGANISM: Artificial Sequence
<220> FEATURE:
<223> OTHER INFORMATION: forward primer

<400> SEQUENCE: 2
cagcggctgc tttatattcc                                                     20

<210> SEQ ID NO 3
<211> LENGTH: 20
<212> TYPE: DNA
<213> ORGANISM: Artificial Sequence
<220> FEATURE:
<223> OTHER INFORMATION: reverse primer

<400> SEQUENCE: 3
ggcacggctc ttgttgtagt                                                     20
```